United States Patent [19]
Fujiwara et al.

[11] Patent Number: 5,112,486
[45] Date of Patent: May 12, 1992

[54] MACHINE ELEMENT FOR USE IN LIQUID TREATING SYSTEM

[75] Inventors: Goro Fujiwara; Mitsunobu Masuda; Masanori Shiraishi; Nobuya Matsumoto, all of Osaka, Japan

[73] Assignees: Takuma Co., Ltd.; Suntory Limited, both of Osaka; Shinanen New Ceramic Corporation, Tokyo, all of Japan

[21] Appl. No.: 545,763

[22] Filed: Jun. 28, 1990

Related U.S. Application Data

[63] Continuation of Ser. No. 308,685, Feb. 9, 1989, abandoned.

[30] Foreign Application Priority Data

Feb. 12, 1988 [JP] Japan .................. 63-31507

[51] Int. Cl.⁵ ........................... B01D 36/00
[52] U.S. Cl. ................... 210/416.1; 210/501
[58] Field of Search .......... 106/15.05; 210/501, 210/502, 348, 416.1; 424/618

[56] References Cited

U.S. PATENT DOCUMENTS 4,076,622  2/1978  Costin ..................... 424/618
4,107,046  8/1978  Corder .................... 210/282
4,603,152  7/1986  Laurin et al. ............ 106/15.05

FOREIGN PATENT DOCUMENTS 2102912  8/1972  Fed. Rep. of Germany .
2316668  10/1973  Fed. Rep. of Germany .
3001674  7/1981  Fed. Rep. of Germany .
2087553  12/1971  France .
148842  10/1931  Switzerland .
2097376  11/1982  United Kingdom .

OTHER PUBLICATIONS

Patent Abstracts of Japan (Apr. 15, 1988) vol. 12, No. 122.
Patent Abstracts of Japan (Apr. 4, 1986) vol. 10, No. 85.
Patent Abstracts of Japan (May 29, 1986) vol. 10, No. 148.

Primary Examiner—Ivars Cintins
Attorney, Agent, or Firm—Felfe & Lynch

[57] ABSTRACT

Disclosed is a machine element for use in a liquid treating system. The machine element has an antibacterial property at least at a portion thereof which is to come into contact with the treated liquid in the course of system operation.

3 Claims, 2 Drawing Sheets

MACHINE ELEMENT FOR USE IN LIQUID TREATING SYSTEM

This application is a continuation of application Ser. No. 308,685, filed Feb. 9, 1989, now abandoned.

BACKGROUND OF THE INVENTION

1. FIELD OF THE INVENTION

The present invention relates to a machine element such as a pipe, a tank or a coupler, a valve or the like to be attached to the pipe and tank for use in a liquid treating system, and more particularly to an art of eliminating micro-organisms from or sterilizing the system.

2. DESCRIPTION OF THE PRIOR ART

In a system for treating pure water, it is necessary to suppress propagation of micro-organisms. Similarly, in a system for treating sea water or cooling water, it is desired to suppress propagation of various marine organisms such as sea shell embryos.

However, in the pure water treating system, residual chlorine is eliminated e.g. in the course of a demineralizing process, which elimination necessarily results in undesirable propagation of micro-organisms at the water-transporting pipes or water-reserving tanks. In view to this problem, the prior art has suggested providing an ultraviolet sterilizer or an ultrafilter at such portions as above where the propagation of micro-organisms is most likely to occur. However, the effect of the sterilizer or the filter extends only within the vicinity of the unit and there still occurs organism propagation outside the vicinity. Then, in the conventional pure-water treating system, it has been a common practice to regularly sterilize the entire system passage by flushing a hot water or a diluted solution of formalin, hydrogen peroxide or the like (e.g. "Manufacturing Method of Pure Water and Superpure Water" published by Sachi Shobo).

However, the above method has some drawbacks to be described next. First, the flush-sterilizing treatment of the entire system passage requires a great deal of treatment chemical or an additional device for feeding the hot water, thereby inviting cost increase in the entire system. Second, while the treatment is being carried out, the operation of the sytem must be stopped, thereby deteriorating the system operational efficiency. Third, the effect of the treatment lasts only temporarily. That is, after a lapse of certain time period, the micro-organism propagation occurs again. Fourth, the sterilizing treatment liquid often fails to reach intricate portions of the system such as a curved piping, coupler, valve or a bolt hole, where the micro-organisms tend to remain un-sterilized and propagates significantly.

In the sea-water treating system for desalinating sea water, it has been a common practice to add chlorine to the sea water in order to suppress adherence to or growth of embryo shells on interior walls of a sea-water inlet pipe or the like (e.g. "Kogyo-yosui Binran" published by Sangyo Tosho Corp.).

However, the addition of the chlorine has an adverse influence on a polyether type reverse osmosis filter often employed in such desalinating system. Therefore, immediately before the reverse osmosis filter, a neutralizing treatment must be effected on the free chlorine in the sea water by sodium hydrogensulfite. Therefore, this method also invites system cost increase due to the addition of neutralizing liquid or unit for feeding the same.

The primary object of the present invention is to provide a machine element for use in a liquid treating system which may suppress undesirable propagation of micro-organisms inside the system for an extended period of time.

SUMMARY OF THE INVENTION

For accomplishing the above-noted object, according to a machine element for use in a liquid treating system, the element comprises a liquid-contact portion provided with an antibacterial property.

The antibacterial property is defined herein as such property as to prevent growth of or to suppress propagation of micro-organisms.

Next, functions and effects of the machine element of the invention will be particularly described.

The machine element may acquire such antibacterial property in various ways. That is, if the element is of a metal, the element may be lined or coated with a layer of antibacterial resin material. If the element is of a resin, its base resin material may be mixed with an antibacterial additive. Then, if these machine elements are employed at positions of the system where the treatment liquid is delivered or reserved, the liquid may be placed in a constant contact with the antibacterial faces of the elements, whereby growth or propagation of micro-organisms may be advantageously prevented.

In comparison with the prior methods, the present invention is advantageous in that the desired antibacterial property may be readily provided at the intricate positions of the system such as a curved piping, coupler, valve or a bolt hole where the treatment liquid hardly arrives in the prior art.

As the result, according to the present invention, the suppression and prevention of growth and propagation of micro-organisms in a liquid treating system may be readily and efficiently achieved by providing the antibacterial property to the system-constituting machine elements per se without employing any additional devices or means. That is, with the present invention, the desired antibacterial effect may be achieved in the course of normal system operation as the running liquid comes into contact with the antibacterial faces of the machine elements. Further, even if there occurs a bacterial contamination from the exterior of the system, the invaded bacteria may be eliminated or suppressed in its propagation as the normal system operation progresses, whereby the system may operate under properly sterilized condition for a long time period. Then, the present invention has overcome the aforenoted drawbacks of the prior art, i.e. the necessity of flush-cleaning operation and the interruption of system operation associated therewith, and the requirements of additional device and chemicals for the sterilizing treatment. Accordingly, with the machine element of the present invention, there may be achieved a low-cost liquid treating system for treating pure water, sea water or the like which may run efficiently and inexpensively under the sterilized condition without interruptions for maintenance for a long time.

Other features, functions and objects of the present invention will become apparent from the following detailed description of preferred embodiments with reference to the accompanying drawings.

BRIEF DESCRIPTION OF THE DRAWINGS

Accompanying drawings FIGS. 1 through 4 illustrate preferred embodiments of the present invention; in which, FIG. 1 is a schematic of a pure-water treating system, FIG. 2 is a section of a coupler as one example of a machine element related to the present invention, FIG. 3 is a schematic of a sea-water treating system, and FIG. 4 is a schematic of a cooling-water treating system.

DESCRIPTION OF PREFERRED EMBODIMENTS

A machine element related to the present invention for use in a liquid treating system will be particularly described hereinafter with reference to the accompanying drawings.

Figure 1:
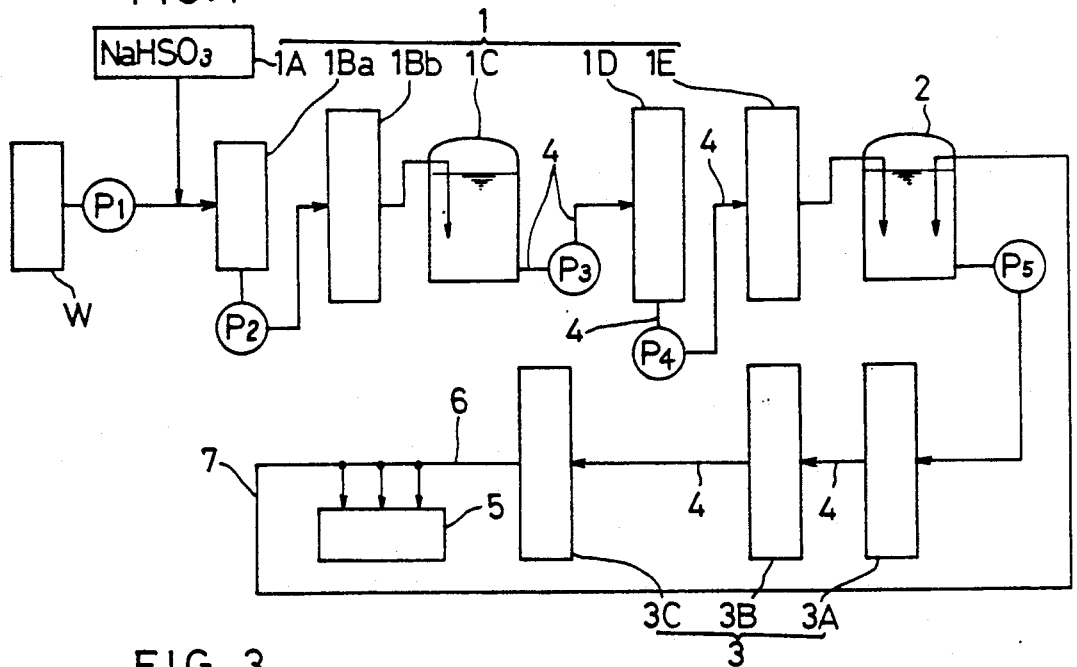

In FIG. 1, there is shown a pure-water treating system for obtaining pure water for cleaning IC components in the electronics industry or for medical applications.

This pure-water treating system comprises, as main components thereof, a primary treating device 1 for obtaining a primary water from a raw material water W, a primary water tank 2 for reserving the primary water, a secondary treating device 3 for processing the primary water from the primary water tank 2 into a secondary pure water, a piping 4 for transporting the water between the respective components 1, 2 and 3, a further piping 6 for distributing the secondary water from the secondary treating device 3 to respective use points 5, and a plurality of pumps P1 through P5 for pumping the water.

Next, the respective system components will be specifically described.

The primary treating device 1 includes a neutralizing agent introducing device 1A for introducing into a commercial water as the raw material water W sodium hydrogensulfite ($NaHSO_3$) for neutralizing free chlorine existent in the water, a filter 1Bb for eliminating most of ions and fine solid particles in the water, a reverse osmosis film module 1Bb formed of a polyamido film, a filtered-water tank 1C for reserving the water filtered through the reverse osmosis film, a vacuum degassing tower 1D for eliminating residual oxygen gas, carbon dioxide gas or the like from the water pumped from the filtered-water tank 1C and an ion exchange equipment 1E for eliminating residual ions at the final stage of the primary treatment operation.

The secondary treating device 3 includes an ultraviolet ray sterilizing lamp 3A for sterilizing the primary water from the tank 2 by ultraviolet ray, a polisher 3B for removing the entire ions, and an ultrafilter film 3C for eliminating residual fine solid particles to a few units per cubic centimeter at the final stage of the secondary treatment operation.

Incidentally, in the secondary water from the secondary treating device 3, if the water is kept still, there often occurs propagation of micro-organisms therein and also a reverse ion exchange phenomenon is likely to occur at the polisher 3B of the secondary treating device 3. For these reasons, this secondary water is constantly circulated between the device 3 and the primary water tank 2 by way of a circulating passage 7.

According to the present invention, in the pure-water treating system described above, various unillustrated machine elements such as couplers, valves and bolts attached or connected to the above system components i.e. the treating devices 1 and 3, primary water tank 2, pipings 4, 6 and 7 and the pumps P1 through P5 are provided with an antibacterial property at their water-contact faces.

More particularly, these machine elements are formed mainly of resin. In molding these elements, an inorganic antibacterial agent is added to the base pellet containing polyvinylchloride, resin, plasticizing agent and stabilizing agent so that the formed water-contact faces of the elements may acquire the antibacterial property.

The above inorganic antibacterial agent is manufactured by bonding a natural or synthetic ion exchanger or zeolite with a metal ion of Ag, Cu, Zn, Sn or the like and stabilizing the same thereafter. One known example of such agent is available under a commercial name of "antibacterial zeomic" manufactured by Shinanen New Ceramic Corp.

The adding amount of the inorganic antibacterial agent should preferably range between 0.01 and 25 wt. % relative to the total amount of employed resin material.

If these machine elements are used in the purewater treating system described hereinbefore, with the normal system operations of transporting or reserving the water therewithin, the treatment-object water constantly comes into contact with the interior faces having the antibacterial property of the various system components 4, 6, 7, 1C and 2, whereby growth or propagation of the micro-organisms existent in the water may be effectively prevented. Accordingly, the system may operate to treat the pure water under properly sterilized condition for a long time period without any additional means or devices for sterilizing treatment or without being interrupted in its operation for maintenance.

Further, even if some micro-organisms invade the system externally at e.g. the tanks 1C and 2, these invaded micro-organisms may be effectively eliminated as they come into contact with the interior faces of the tanks or of the pipings 2 and 3 in the course of system operation. Therefore, in this case also, the system may maintain its sterilized or substantially sterilized condition.

An experiment was conducted in order to investigate the effect of the invention's machine elements having the antibacterial property.

In this experiment, in the pure-water treating system, some of the machine elements were provided with the antibacterial property according to the invention while others were not (in the table below, elements are denoted by "with antibacterial agent" and "without antibacterial agent", respectively). Then, these elements were disposed in pipe sections delivering the primary water, then, the primary water was caused to flow at a constant flow rate through the closed pipe sections. After lapses of 10 days, 30 days, 45 days and 60 days respectively, the pipe sections were taken out of the system and were vibrated with a sterilizing water therein. The sampled waters were placed on TGE culture mediums and cultured thereon for 48 hours. Then, visual observations were made for checking existance of micro-organisms. The experiments results show the distinguished and long-lasting effect of the machine elements of the invention.

TABLE 1

| | existence of micro-organisms | |
|---|---|---|
| days | with antibacterial agent | without the agent |
| 10 | none | none |
| 30 | none | detected |
| 45 | none | detected |
| 60 | none | detected |

Some alternate embodiments will be described next.

(1) In the previous embodiment, the machine elements of the invention comprise the pipings 4, 6 and 7, tanks 1C and 2, pumps P1 through P5, valves, couplers and bolts. Alternatively, the machine elements may include all other system components which may come into contact with the treatment-object liquid. For example, the invention may be applied to a container for transporting the liquid.

Further, the present invention may be applied to various machine elements for use in other systems which should be sterilized for preventing growth or propagation of micro-organism within the system. Some examples of such system are a transport system for transporting containers of food stuff, drinks, medicines or the like and a transport system for transporting food stuff in a food-processing industry.

(2) The present invention may be embodied as sealing members such as packings, O-rings, gaskets for preventing leakage of liquid at connections between pipes, containers and valves.

Figure 2:
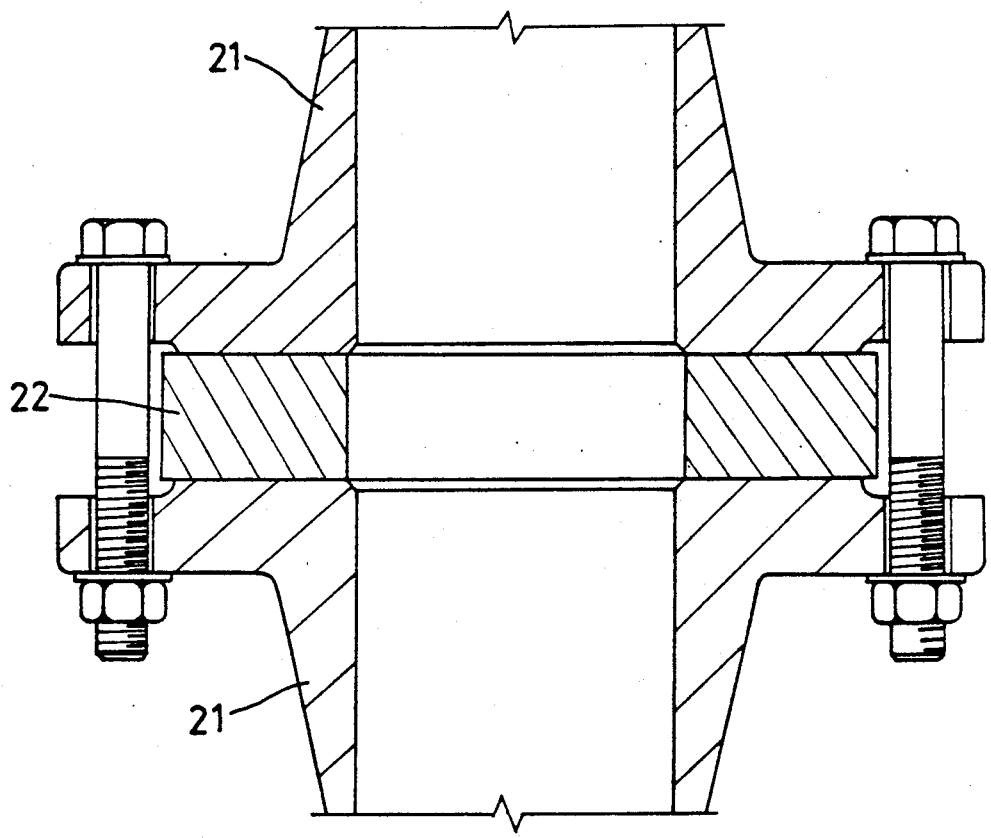

For example, FIG. 2 shows a gasket 22 to be disposed between a pair of connecting flanges 21. This gasket 22 is formed of ethylene propylene rubber mixed with an antibacterial powder. In the case of this gasket 22, the antibacterial property is provided to the entire surface of the gasket.

As the antibacterial agent for providing the antibacterial property, a synthetic zeolite as an example of ion exchangers added with Ag ion, Zn ion or the like is used.

Some specific manufacturing experiments of the agent will be described hereinafter.

EXPERIMENT 1

(i) Production of Sample Materials

A synthetic zeolite, as an ion exchanger, was added by 2.5 to 3 wt. % of Ag ion and Zn ion by ratio of 1:3. This mixture was dried and pulverized to 1 µm to 2 µm particle diameter. This pulverized mixture was added to three resin plates A, B and C by 2 wt. %, 6 wt. % and 0 wt. %, respectively. The physical dimensions of these resin plates A, B and C were measured respectively to be 1 cm × 1 cm × 3 mm.

(ii) Preparation of Sample Liquid

Pseudomonas sp. isolated from a desalinated commercial water were cultured on a standard type TGE culture medium for two days at 25 degrees Celsius. Then, to 20 ml of this the cultured liquid, 980 ml of pure water was added, and the mixutre was stirred well, whereby a sample liquid was obtained.

(iii) Processes

Into the above sample liquid, the three kinds of resin plates A, B and C were introduced and were caused to stand for 6 days at the room temperature. Then, the resin plates A, B and C were taken out of the liquid and dried. The surfaces of these dried resin plates were observed through a scanning electron microscope.

(iv) Results

As shown in Table 2 below, the surface of the sample material C without addition of synthetic zeolite pulverized material was covered in its entirety with micro-organisms. On the other hand, the surfaces of the other sample materials A and B with the addition of synthetic zeolite pulverized material were only slightly and partially covered with micro-organisms. This shows the distinguished antibacterial effect of the synthetic zeolite pulverized material.

TABLE 2

| sample materials | results |
|---|---|
| resin plate A (2% mixture) | micro-organisms observed on 20% of entire area |
| resin plate B (6% mixture) | substantially same as A |
| resin plate C (0% mixture) | micro-organisms observed on entire area |

EXPERIMENT 2 i Production of Sample Materials

A synthetic pulverized zeolite material manufactured by the same processes as in the Experiment 1 was added to three FRP resin plates A', B' and C' by 2 wt. %, 6 wt. % and 0 wt. %, respectively. The FRP resin plates A', B' and C' were measured respectively to be 5 cm × 5 cm × 5 mm.

ii Preparation of Sample Liquid

As a sample liquid, a Pseudomonas sp. liquid (cell population: $10^5$/ml) was prepared.

iii Processes

Onto the three kinds of FRP resin plates A', B' and C', 1 ml of the above sample liquid was dropped and the plates were caused to stand for 18 hours at 37 degrees Celsius. Then, the liquid was washed off the surfaces of the plates by physiological salt solution. Measurements were conducted for obtaining the numbers of living cells contained in the respective solutions washed off the plates.

iv Results:

As shown in Table 3 below, in the case of the solutions from the materials with the addition of synthetic zeolite pulverized material, the numbers of living cells were less than 1/100 to 1/1000 relative to that of the solution obtained from the resin material without addition of synthetic zeolite pulverized material. This again shows the distinguished antibacterial effect of the synthetic zeolite pulverized material.

TABLE 3

| sample materials | number of living cells |
|---|---|
| resin plate A' (2% mixture) | 2 × 10 |
| resin plate B' (6% mixture) | 1 × 10 |
| resin plate C' (0% mixture) | 3 × 10 |

As may be apparent from the above experiment results, if the liquid-contact face is provided with the antibacterial property, this may prevent or suppress growth and propagation of micro-organisms in the liquid.

(3) As the method of providing the desired antibacterial property to the liquid-contact faces of machine elements for use in a liquid treating system, in addition to the method described in the previous embodiment, it is also possible to line the inner faces of the element with a lining material made from an antibacterial agent or to coat the same with a layer made of such antibacterial agent. In these cases, it is also possible to provide the antibacterial property to those machine elements which are already installed in a liquid treating system.

(4) As described hereinbefore, the machine element of the invention may be employed in various liquid treating systems besides the pure-water treating system described in the previous embodiment. Some such applications of the invention's element will be specifically described next.

Figure 3:
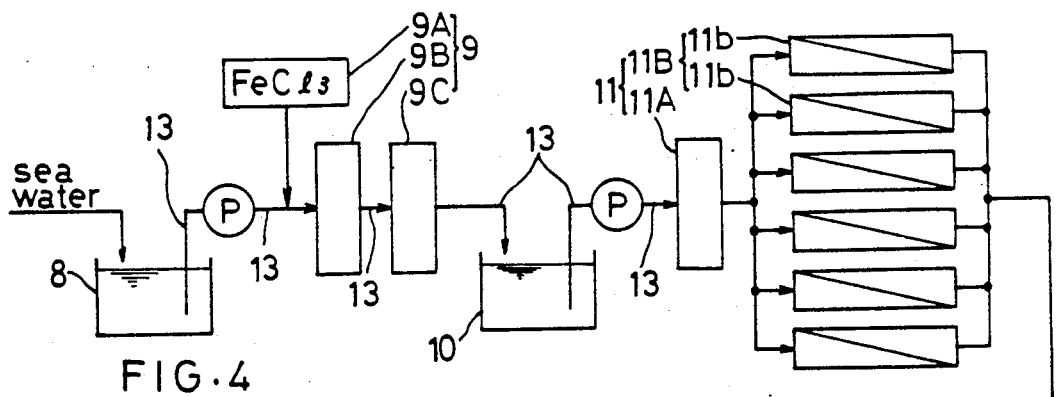

(4-1) FIG. 3 shows a sea-water treating system as an example of system for obtaining fresh water from sea water.

This sea-water treating system comprises, as main components thereof, a sea water reservoir 8 for reserving pumped-up sea water, a primary treating device 9 including a coagulant injecting device 9A for injecting into the sea water at the reservoir 8 ferric chloride ($FeCl_3$) as a coagulant for eliminating suspended solids existent in the sea water, a filter 9B and a degassing device 9C, a primary water tank 10 for reserving a primary water from the primary treating device 9, a secondary treating device 11 including a pressure pump 11A and a desalinating device 11B having a plurality of reverse osmosis film modules 11b for desalinating the primary water fed with pressure from the pump by causing the water to permeate the modules, a secondary water tank 12 for reserving the desalinated secondary water from the secondary treating device 11 and a piping 13 for transporting the water between the respective components 9, 10, 11 and 12.

In the above sea-water treating system, according to the present invention, a plurality of pipes constituting the piping 13 are formed as FRP pipes made of a resin material such as polyester, vinylester, epoxy mixed with the inorganic antibacterial agent described in the foregoing embodiment.

With the above arrangement, growth or propagation of micro-organisms contained in the sea water may be effectively prevented or suppressed.

Accordingly, it becomes possible to reduce in amount or to entirely eliminate the addition of chlorine to the sea water, which has been commonly practiced in order to suppress adherence to or growth of sea shell embryo on interior walls of a sea-water inlet pipe or the like but which has an adverse influence on the reverse osmosis filters. As the result, system maintenance costs may be advantageously reduced.

Figure 4:
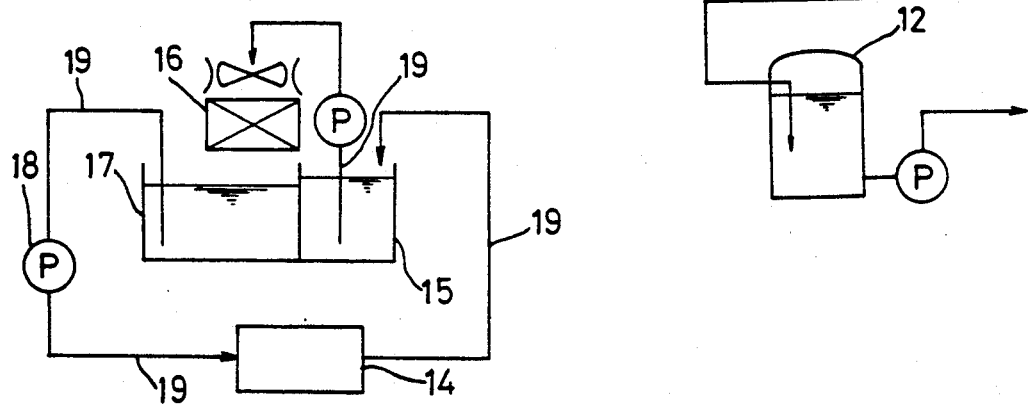

(4-2) FIG. 4 shows a cooling-water treating system for circulating a cooling water used for air-conditioning.

This cooling-water treating system comprises, as main components thereof, a recycled-water tank 15 for reserving a water recycled from a load 14 such as of a factory, a cooling tower 16 for carrying out a heat-exchange operation of the recycled water pumped from the tank 15, a tank 17 for reserving the water after the heat-exchange operation, a pressure pump 18 for pressure-feeding the water from the tank 17 again to the load 14, and a piping 19 for transporting the water between the respective components 14 through 18.

In this cooling-water treating system, according to the present invention, the piping 19 and the tanks 15 and 17 are formed of the same antibacterial-agent-mixed resin material as used in the foregoing embodiment.

The above arrangement may effectively suppress propagation of micro-organisms in the circulated cooling water thereby preventing development of slime at the piping 19 and tanks 15, 17. Accordingly, the injection of chlorine or chalcocite may be drastically reduced in amount or becomes utterly unnecessary. As the result, the running costs of the system may be advantageously reduced.

(4-3) Besides the above-specified applications, the machine elements of the invention for use in a liquid treating system may be employed in various installations for treating various kinds of industrial waters or for processing an ion exchanger refined water for use in cosmetics.

(5) As the antibacterial agent, it is possible to use a cation exchange resin having its part or all of ion exchange groups substituted by Ag ions.

In this case, the cation exchange resin may comprise ABS resin or one or a combination of polystyrene gel type strong acid cation exchange resin, polystyrene macroporous type strong acid cation exchange resin, polyolefin resin phenol type strong acid cation exchange resin, and a weak acid cation exchange resin.

In case the antibacterial agent comprises a cation exchange resin having portion of ion exchange groups substituted by Ag ions, the remaining exchange groups may be sodium bonded with monovalent ion or may be zinc, tin, copper bonded with two or more valence metal ions.

In comparison with the natural or synthetic zeolite, the above-described antibacterial agent is advantageous in that there occurs less granulation. As the result, if this antibacterial agent is contained in the column, there will occur less clogging or fall-out trouble.

Moreover, the above column filled with this antibacterial agent will have less inpurity in comparison with zeolite, especially the natural zeolite. Therefore, this will be more suitable as the antibacterial agent for use with treatment of pure or superpure water.

What is claimed is:

1. In a liquid treating system comprising liquid contacting structural machine elements of packings, o-rings, gaskets, films, plates, valves, filters, couplers, connectors, pipes, bolts, sealing members, pumps, couples and containers the improvement wherein a liquid-contact portion of at least one of said structural machine elements consists of a resin material having antibacterially active zeolite fine particles bonded with at least two metal ions selected from the group consisting of Ag and Zn ion in a ratio of about 1:3 or Ag ion with remaining exchange groups bonded with Na, Sn or Cu.

2. The liquid treating system as defined in claim 1, wherein said resin material forming the liquid-contact portion of the structural machine elements of the system is a resin selected from at least one of the group consisting of polystyrene resin, polyvinylchloride resin, polyolefin resin, phenol-type strong acid cation exchange resin, weak acid cation exchange resin, ABS resin and FRP resin.

3. The liquid treating system of claim 2 wherein said resin consists of from 0.01 to 25 wt % of said antibacterially active zeolite fine particles relative to said resin.

* * * * *